US008083714B2

(12) United States Patent
Quint

(10) Patent No.: US 8,083,714 B2
(45) Date of Patent: Dec. 27, 2011

(54) CATHETER BALLOON

(75) Inventor: Bodo Quint, Rottenburg/Seebronn (DE)

(73) Assignee: Abbott Laboratories Vascular Enterprises Limited, Dublin (IE)

( * ) Notice: Subject to any disclaimer, the term of this patent is extended or adjusted under 35 U.S.C. 154(b) by 870 days.

(21) Appl. No.: 10/303,951

(22) Filed: Nov. 26, 2002

(65) Prior Publication Data

US 2003/0100915 A1 May 29, 2003

(30) Foreign Application Priority Data

Nov. 28, 2001 (EP) .................................. 01128260

(51) Int. Cl.
*A61M 31/00* (2006.01)
(52) U.S. Cl. ............... 604/103.06; 606/194; 604/916; 604/103.07; 604/103.14; 604/509
(58) Field of Classification Search ............ 606/194; 604/916, 103.14, 509, 103.06–103.07
See application file for complete search history.

(56) References Cited

U.S. PATENT DOCUMENTS 5,041,125 A * 8/1991 Montano, Jr. .................. 606/192
5,853,389 A * 12/1998 Hijlkema ................. 604/103.07
6,013,055 A * 1/2000 Bampos et al. .......... 604/103.07
6,652,485 B1 * 11/2003 Gaudoin et al. ......... 604/103.07

FOREIGN PATENT DOCUMENTS

EP 0 783 897 A2 7/1997

* cited by examiner

*Primary Examiner* — Gary Jackson
*Assistant Examiner* — Diane Yabut
(74) *Attorney, Agent, or Firm* — Workman Nydegger

(57) ABSTRACT

A catheter balloon is configured to improve its fold-in or collapsing behavior. The catheter balloon has a balloon body portion, a first tapered end portion and a second tapered end portion. The balloon body portion has a substantially cylindrical shape in an expanded state. The first tapered end portion is formed at a first end of the balloon body portion. The first tapered end portion includes a first predetermined embossment. The second tapered end portion is formed at a second end of the balloon body portion. The second tapered end portion includes a second predetermined embossment. The balloon body portion is formed free of a predetermined embossment. In other words, the balloon body portion is formed without folds so that there is only predetermined folding on the conical end portions for inducing the folding of the balloon body portion in a predetermined direction upon collapsing.

9 Claims, 2 Drawing Sheets

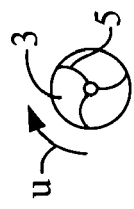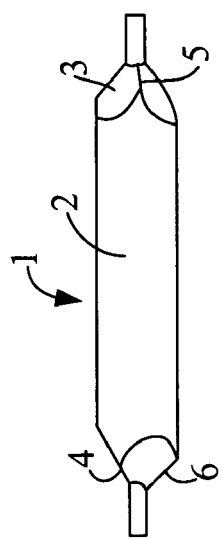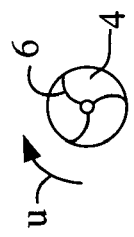
Fig. 3  Fig. 1  Fig. 4
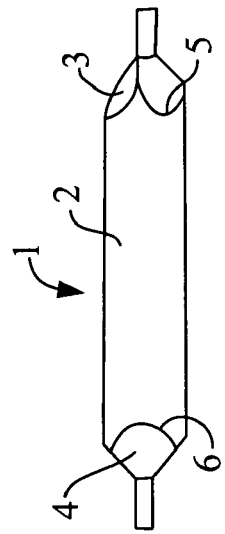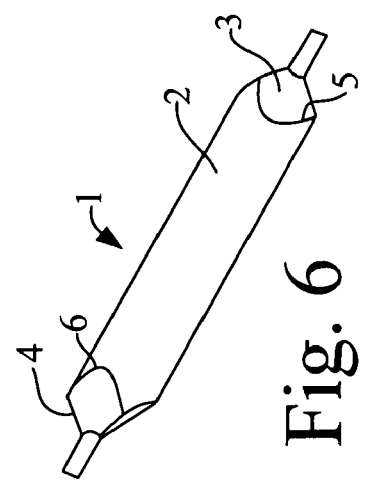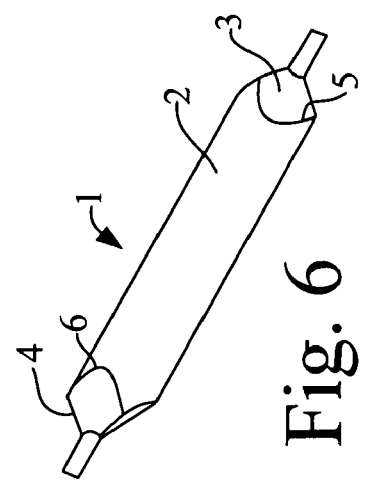
Fig. 2  Fig. 5  Fig. 6

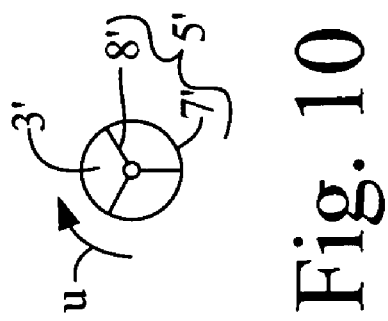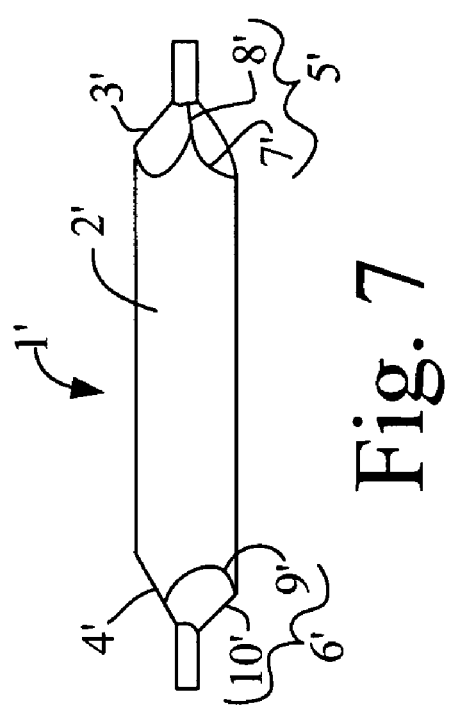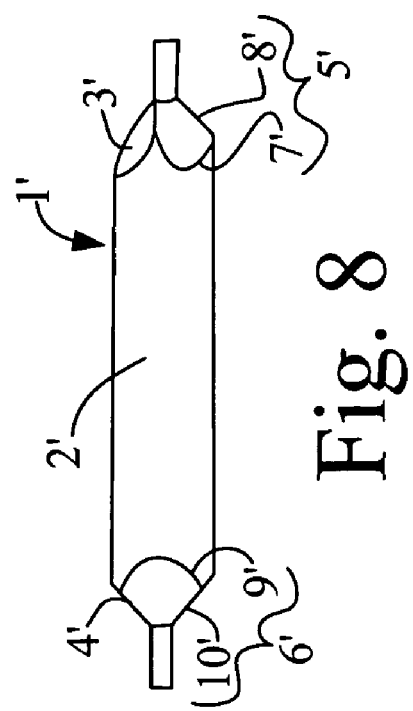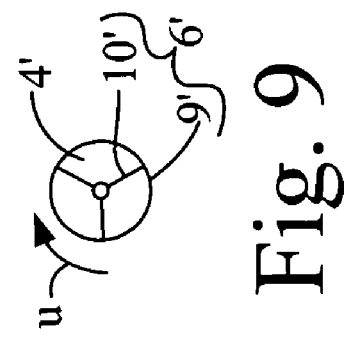
Fig. 10
Fig. 7
Fig. 8
Fig. 9

CATHETER BALLOON

BACKGROUND OF THE INVENTION

1. Field of the Invention

The present invention generally relates to a catheter balloon. More specifically, the present invention relates to a catheter balloon with improved collapsing or fold-in behavior.

2. Background Information

One example of a catheter balloon is disclosed in U.S. Pat. No. 5,853,389. The catheter balloon comprises a collapsible balloon body which must be placed on a catheter shaft such that it occupies as little space as possible prior to its expansion. To this end the catheter balloon, as well as its tapered end portions, are provided with foldings. Apart from the property that the catheter balloon should have a minimal profile in the area of the balloon in order to be guided, for example, through a stenoses in an easy way, tests performed within the scope of the invention have shown that when a folding is provided on the balloon body and on the tapered ends, the behavior during folding-in or collapsing is in need of improvement. In particular it has been found that the reversibility of the balloon into its folded condition poses a problem, for the balloon loses its memory behavior with respect to the original folding due to the cycle of inflation and deflation and the accompanying mechanical load. This may, for example, give rise to great difficulties when the balloon is guided through two successive stenoses. When the balloon is deflated after expansion of the first stenoses and if a different folding that is not identical with the first folding is created due to the loss in memory behavior, it may happen that the balloon in the second stenoses is blocked during retraction because the original folding that enables the passage through the stenoses is in fact not achieved anymore.

In view of the above, it will be apparent to those skilled in the art from this disclosure that there exists a need for an improved catheter balloon. This invention addresses this need in the art as well as other needs, which will become apparent to those skilled in the art from this disclosure.

SUMMARY OF THE INVENTION

It is therefore the object of the present invention to provide a catheter balloon, which permits a better collapsing or fold-in behavior than that offered by the balloon known in the prior art.

This object is basically achieved by a catheter balloon that basically includes a balloon body portion, a first tapered end portion and a second tapered end portion. The balloon body portion has a substantially cylindrical shape in an expanded state. The first tapered end portion is formed at a first end of the balloon body portion. The first tapered end portion includes a first predetermined embossment. The second tapered end portion is formed at a second end of the balloon body portion. The second tapered end portion includes a second predetermined embossment. The balloon body portion is formed free of a predetermined embossment. In other words, the balloon body portion is formed without folds so that there is only predetermined folding on the conical end portions for inducing the folding of the balloon body portion in a predetermined direction upon collapsing.

In the catheter balloon according to the present invention the tapered end portions alone are provided with a shape that supports a back-folding into the original state. An improved folding-in or collapsing is accomplished during deflation because, in contrast to the prior art in which the balloon body portion is also provided with folds or ribs, predetermined embossment lines do not act on the balloon body portion of the balloon according to the invention. This is possible because the balloon body portion is formed without any embossments.

For a better understanding of the present invention it should be noted that "folding" of a catheter balloon means a step after balloon manufacture. During manufacture the balloon is already manufactured with a shape or embossment in the tapered conical end portions that produces different wall thicknesses in the respective cone portion. These different wall thicknesses and geometries are to enhance the "folding back" into a multiple folding. This is perfected in the catheter balloon according to the invention by the fact that the balloon body itself is without any predetermined embossment.

Hence, since in the catheter balloon of the invention only the tapered or conical end portions are provided with a predetermined embossment, embossment lines of said embossments will induce the folding of the main body, so that the above-mentioned improved folding characteristics are achieved.

Since the folding on an end portion, when viewed from the top, is not congruent with the folding provided on the other end portion, but is offset relative thereto in circumferential direction, this entails the advantage that the balloon body is folded in a defined direction. This considerably increases the probability of a back folding into a defined state, which is identical with the original folding, for the provision of the offset of the embossments on the two end portions yields a slightly twisted shape of the embossment folds, so that these will fold back in the defined and identical direction, whereby the balloon will take on its original shape and dimension that prevents blockage in a stenoses.

Thanks to the above-explained offset which extends from the distal to the proximal end of the balloon body, a slight twist is produced in addition, which predetermines the direction in which the folds of the catheter balloon can escape when hitting upon an obstacle.

These and other objects, features, aspects and advantages of the present invention will become apparent to those skilled in the art from the following detailed description, which, taken in conjunction with the annexed drawings, discloses a preferred embodiment of the present invention.

BRIEF DESCRIPTION OF THE DRAWINGS

Referring now to the attached drawings which form a part of this original disclosure:

FIG. 1 is a schematically simplified front elevational view of a catheter balloon according to the present invention;

FIG. 2 is a top plan view of the catheter balloon illustrated in FIG. 1 in accordance with the present invention;

FIG. 3 is a first axial end elevational view of the catheter balloon illustrated in FIGS. 1 and 2 to show a first conically tapered end portion in accordance with the present invention;

FIG. 4 is a second axial end elevational view of the catheter balloon illustrated in FIGS. 1-3 to show a second conically tapered end portion in accordance with the present invention;

FIG. 5 is a perspective view of the catheter balloon illustrated in FIGS. 1-4 in accordance with the present invention;

FIG. 6 is a perspective view of the catheter balloon illustrated in FIGS. 1-5 in accordance with the present invention.

FIG. 7 is a schematically simplified front elevational view of another embodiment of a catheter balloon according to the present invention;

FIG. 8 is a top plan view of the catheter balloon illustrated in FIG. 7 in accordance with the present invention;

FIG. 9 is a first axial end elevational view of the catheter balloon illustrated in FIGS. 7 and 8 to show a first conically tapered end portion in accordance with the present invention;

FIG. 10 is a second axial end elevational view of the catheter balloon illustrated in FIGS. 7-9 to show a second conically tapered end portion in accordance with the present invention;

DETAILED DESCRIPTION OF THE PREFERRED EMBODIMENTS

Selected embodiments of the present invention will now be explained with reference to the drawings. It will be apparent to those skilled in the art from this disclosure that the following descriptions of the embodiments of the present invention are provided for illustration only and not for the purpose of limiting the invention as defined by the appended claims and their equivalents.

Referring initially to FIGS. 1 and 2, a catheter balloon 1 is illustrated in accordance with a first embodiment of the present invention. The catheter balloon 1 basically comprises a balloon body portion 2 which is substantially cylindrical in the expanded state between first and second ends of the balloon body portion 2. The balloon body portion 2 is a hollow tubular member that is expanded and contracted in a conventional manner. The ends of the balloon body portion 2 are provided with conically tapered end portions 3 and 4. The first conically tapered end portion 3 includes a first predetermined embossment 5. The second conically tapered end portion 4 includes a second predetermined embossment 6. These predetermined embossments 5 and 6 are lines or ridges that are imprinted or stamped into the balloon material along the end portions 3 and 4. In other words, the predetermined embossments 5 and 6 are predetermined surface structures featuring ribs or fold lines or the like that are formed by areas of thin material due to the imprinting or stamping at the balloon material.

The conically tapered end portions 3 and 4 are preferably integrally formed with the balloon body portion 2 as a one-piece, unitary member using conventional manufacturing techniques, e.g., blow-molding process. The catheter balloon 1 is constructed of any known materials that can be used as a catheter balloon. In any event, the catheter balloon 1 is preferably constructed of a flexible material, such as nylon, that can be collapsed, folded, and expanded again afterwards by increasing the pressure inside the catheter balloon 1.

As illustrated by FIGS. 1, 2, 5 and 6, the balloon body portion 2 is formed without any embossments, folds or ribs. Thus, the balloon body portion 2 is formed free of a predetermined embossment, folds or ribs. Preferably, the balloon body portion 2 has a uniform, constant radial thickness. The end portions 3 and 4 have a plurality of spiral or curved lines representing the embossments 5 and 6. As seen in FIGS. 3 and 4, the predetermined embossment 5 of the first conically tapered end portion 3 is circumferentially offset relative to the folding lines or predetermined embossment 6 of the second conically tapered end portion 4, when viewed in a circumferential direction U. This entails the advantage that upon collapsing or folding of the catheter balloon 1, the embossments 5 and 6 induce a folding of the balloon body portion 2 in a defined predetermined direction.

In an alternate configuration shown in FIGS. 7, 8, 9 and 10, the catheter balloon 1' basically includes a balloon body portion 2'. The ends of the balloon body portion 2' are provided with conically tapered end portions 3' and 4'. The first conically tapered end portion 3' includes a first predetermined embossment 5'. The second conically tapered end portion 4' includes a second predetermined embossment 6'. These predetermined embossments 5' and 6' are lines or ridges that are imprinted or stamped into the balloon material along the end portions 3' and 4'. The predetermined embossments 5' and 6' are predetermined surface structures featuring ribs or fold lines or the like that are formed by areas of thin material due to the imprinting or stamping at the balloon material.

The embossment 5' includes a plurality of curved lines 7' and a plurality of straight lines 8'. The curve lines 7' represent a transition from embossment 5' to the balloon body portion 2'. The straight lines 8' are folds or embossments in the tapering section of the end portions 3'. The embossment 6' includes a plurality of curved lines 9' and a plurality of straight lines 10'. The curve, lines 9' represent a transition from embossment 6' to the balloon body portion 2'. The straight lines 10' are folds or embossments in the tapering section of the end portions 4'.

As seen in FIGS. 9 and 10, the predetermined embossment 5' of the first conically tapered end portion 3' is circumferentially offset relative to the folding lines or predetermined embossment 6' of the second conically tapered end portion 4', when viewed in a circumferential direction U. This entails the advantage that upon collapsing or folding of the catheter balloon 1', the embossments 5' and 6' induce a folding of the balloon body portion 2' in a defined predetermined direction.

The terms of degree such as "substantially", "about" and "approximately" as used herein mean a reasonable amount of deviation of the modified term such that the end result is not significantly changed.

This application claims priority to European Application No. 01 128 260.5. The entire disclosure of European Application No. 01 128 260.5 is hereby incorporated herein by reference.

While only one selected embodiment has been chosen to illustrate the present invention, it will be apparent to those skilled in the art from this disclosure that various changes and modifications can be made herein without departing from the scope of the invention as defined in the appended claims. Furthermore, the foregoing descriptions of the present invention are provided for illustration only, and not for the purpose of limiting the invention as defined by the appended claims and their equivalents. Thus, the scope of the invention is not limited to the disclosed embodiment.

What is claimed is:

1. A catheter balloon comprising:
a balloon body portion having a substantially cylindrical shaped portion in an expanded state between first and second ends of the balloon body portion;
a first tapered end portion formed at the first end of the balloon body portion, the first tapered end comprising a first plurality of converging substantially flattened sections in the expanded state defined by a plurality of first curved embossments entirely surrounding and bounding the periphery of the substantially flattened sections and completely separating the substantially flattened sections from the substantially cylindrical shaped portion, the plurality of first curved embossments curving in a first direction and having a material thickness less than the material thickness of the remainder of the first tapered portion and the balloon body portion; and
a second tapered end portion formed at the second end of the balloon body portion, the second tapered end portion comprising a second plurality of converging substantially flattened sections defined by a plurality of second curved embossments entirely surrounding and bounding the periphery of the substantially flattened sections and completely separating the substantially flattened sections from the substantially cylindrical shaped portion, the plurality of second curved embossments curving in the first direction and having a material thickness less than the material thickness of the remainder of the second tapered portion and the balloon body portion, the plurality of first curved embossments being offset in a circumferential direction relative to the plurality of second curved embossments, the balloon body portion being entirely bounded and surrounded by a first portion of the first curved embossments and by a second portion of the second curved embossments and being formed free of substantially flattened sections and formed free of any structures defining predetermined locations of folding.

2. The catheter balloon according to claim 1, wherein the first plurality of converging substantially flattened sections is offset in a circumferential direction of the balloon body portion relative to the second plurality of converging substantially flattened sections when viewed in an axial direction of the balloon body portion.

3. The catheter balloon according to claim 1, wherein the embossments are formed by imprinting or stamping the balloon material.

4. A catheter balloon for facilitating reversibility from an expanded state to an unexpanded state, the catheter balloon comprising:
   a balloon body portion having a substantially cylindrical shaped portion in an expanded state between first and second ends of the balloon body portion;
   a first tapered end portion formed at the first end of the balloon body portion, the first tapered end comprising a first plurality of converging substantially flattened sections in the expanded state defined by a plurality of connected first spiral embossments surrounding and bounding the substantially flattened sections, each of the first spiral embossments abutting an adjacent first spiral embossment to completely separate the substantially flattened sections from the substantially cylindrical shaped portion, the plurality of first spiral embossments extending in a first direction and having a material thickness less than the material thickness of the remainder of the first tapered portion and the balloon body portion; and
   a second tapered end portion formed at the second end of the balloon body portion, the second tapered end portion comprising a second plurality of converging substantially flattened sections defined by a plurality of connected second spiral embossments surrounding and bounding the substantially flattened sections, each of the second spiral embossments abutting an adjacent second spiral embossment to completely separate the substantially flattened sections from the substantially cylindrical shaped portion, the plurality of second spiral embossments extending in the first direction and having a material thickness less than the material thickness of the remainder of the second tapered portion and the balloon body portion, the plurality of first spiral embossments being offset in a circumferential direction relative to the plurality of second spiral embossments,
   the balloon body portion being entirely bounded and surrounded by a first portion of the first spiral embossments and by a second portion of the second spiral embossments and being formed free of substantially flattened sections and formed free of any structures defining predetermined locations of folding.

5. The catheter balloon according to claim 4, wherein the first plurality of converging substantially flattened sections is offset in a circumferential direction of the balloon body portion relative to the second plurality of converging substantially flattened sections when viewed in an axial direction of the balloon body portion.

6. The catheter balloon according to claim 4, wherein the embossments are formed by imprinting or stamping the balloon material.

7. A catheter balloon comprising:
   a balloon body portion having a substantially cylindrical shape in an expanded state between first and second ends of the balloon body portion;
   a first tapered end portion formed at the first end of the balloon body portion, the first tapered end comprising a first plurality of converging sections in the expanded state defined by a plurality of interconnected first curved embossments, a portion of the first curved embossments forming a thinning boundary about the circumference of the substantially cylindrical shape between the substantially cylindrical shape and the first tapered end portion, the first curved embossments entirely surrounding and bounding the sections, the plurality of first curved embossments curving in a first direction and having a material thickness less than the material thickness of the remainder of the first tapered portion and the balloon body portion; and
   a second tapered end portion formed at the second end of the balloon body portion, the second tapered end portion comprising a second plurality of converging sections defined by a plurality of interconnected second curved embossments, a portion of the second curved embossments forming a thinning boundary about the circumference of the substantially cylindrical shape between the substantially cylindrical shape and the second tapered end portion, the second curved embossments entirely surrounding and bounding the sections, the plurality of second curved embossments curving in the first direction and having a material thickness less than the material thickness of the remainder of the second tapered portion and the balloon body portion, the plurality of first curved embossments and the first plurality of converging sections being offset in a circumferential direction relative to the plurality of second curved embossments and the second plurality of converging sections, respectively,
   the balloon body portion being entirely bounded and surrounded by a first portion of the first curved embossments and by a second portion of the second curved embossments and being formed free of converging sections and formed free of any structures defining predetermined locations of folding.

8. The catheter balloon according to claim 7, wherein the first plurality of sections is offset in a circumferential direction of the balloon body portion relative to the second plurality of sections when viewed in an axial direction of the balloon body portion.

9. The catheter balloon according to claim 7, wherein the embossments are formed by imprinting or stamping the balloon material.

* * * * *